United States Patent [19]
Douglas-Hamilton

[11] Patent Number: 4,690,678
[45] Date of Patent: Sep. 1, 1987

[54] DEVICE AND METHOD FOR FACILITATING ANIMAL ARTIFICIAL INSEMINATION

[75] Inventor: Margaret M. Douglas-Hamilton, Beverly, Mass.

[73] Assignee: 501 Hamilton/Thorn Research Associates, Wenham, Mass.

[21] Appl. No.: 747,912

[22] Filed: Jun. 24, 1985

Related U.S. Application Data

[63] Continuation-in-part of Ser. No. 588,681, Mar. 12, 1984, abandoned.

[51] Int. Cl.[4] .......... A61F 5/00
[52] U.S. Cl. .......... 604/349; 128/79
[58] Field of Search .......... 604/349; 128/79

[56] References Cited

U.S. PATENT DOCUMENTS 3,336,926 8/1967 Gresham .......... 604/349
4,387,726 6/1983 Denard .......... 604/349

FOREIGN PATENT DOCUMENTS 0946822 6/1949 France .......... 604/349

OTHER PUBLICATIONS

Colorado Model Equine Artificial Vagina, Lane Manufacturing Inc., 1982.

*Primary Examiner*—C. Fred Rosenbaum
*Assistant Examiner*—Gene B. Kartchner
*Attorney, Agent, or Firm*—Lahive & Cockfield

[57] ABSTRACT

In an artificial vagina for use in animal artificial insemination that includes a tubular section with an intromission orifice, a thin, flexible plastic sheet liner of a generally cylindrical shape with an intromission opening and a collection chamber is insertable into the artificial vagina, and disposable after one use. A filter mounted on a ring is located within the liner at a reduced diameter portion located intermediate the collection chamber and the main portion of the liner. An external strap frictionally engages the ring to secure the filter.

5 Claims, 4 Drawing Figures

DEVICE AND METHOD FOR FACILITATING ANIMAL ARTIFICIAL INSEMINATION

This application is a continuation-in-part of application Ser. No. 588,681, filed Mar. 12, 1984 now abandoned.

This invention relates to a device and method for facilitating animal artificial insemination, and particularly to devices and methods for improving the use of artificial vaginas in that practice.

In horse and other animal breeding, the method of artificial insemination is frequently used. It is, in fact, being used more frequently, as improvements in devices and methods occur. Artificial insemination offers great advantages to horse breeders by permitting simultaneous fertilization of a number of mares by one stallion, by permitting fertilization of incompetent mares, and by preventing injury to stallions from recalcitrant mares.

In equine and other animal artificial insemination the use of an artificial vagina (AV) is ordinarily required in order to collect the semen from the male animal. After it is used to collect semen from one animal, the AV has to be carefully cleaned and disinfected in order to prevent any possible propagation of disease. The cleaning and disinfecting can take considerable time and effort. Furthermore, the AV is unavailable for use until it is cleaned and disinfected.

Accordingly, it is an object of this invention to provide a device and method for eliminating the time and effort required to clean and disinfect AV's used in artificial insemination procedures for animals. It is another object to provide a device and method that is easy and inexpensive to manufacture and use. It is still another object to provide a device and method that will enhance the sanitary nature of AV's and encourage the use of artificial insemination.

SUMMARY OF THE INVENTION

The invention comprises a disposable artificial vagina (AV) liner and collection receptacle for the collection of semen from a male animal in which the AV comprises a hollow, generally tubular, section having an intromission orifice and an inside wall. The liner comprises a continuous flexible sheet defining a generally tubular main portion having a first end portion and a second end portion. The first end portion defines an intromission opening and the second end portion defines a collection chamber. A filter means is located with the liner intermediate the main portion and the collection chamber, secured to the sheet.

In a preferred embodiment, the continuous flexible sheet includes a reduced diameter portion intermediate the main portion and the collection chamber, the filter means includes a ring means, and the device includes an exterior filter securing means comprising a circumferential strap frictionally engaging the filter ring means through the flexible sheet.

BRIEF DESCRIPTION OF THE DRAWINGS

Other objects, features and advantages of the invention will be pointed out hereinafter or will be inherent in the following description of a preferred embodiment of the invention, including the drawings thereof, in which.

DESCRIPTION OF A PREFERRED EMBODIMENT

Figure 1:
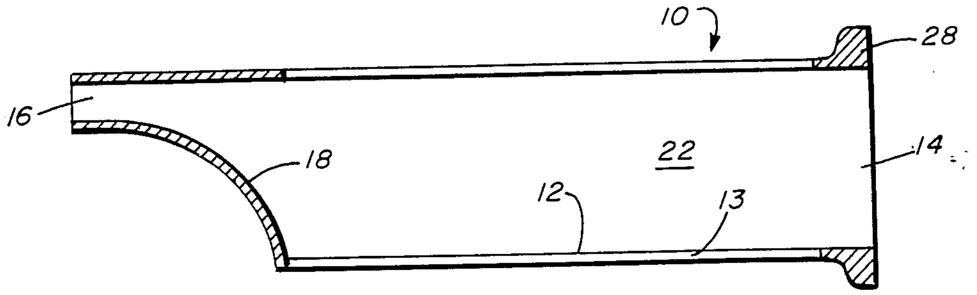
FIG. 1 is a sectional view of a typical AV used in practicing the method of the invention.

The AV shown in FIG. 1 is typical of AV's used in the field of artificial insemination. As illustrated there the AV 10 has a main hollow cylindrically tubular section 12, formed by a wall 13 and having an open intromission orifice 14, and tapering down to an opposite open collection orifice 16.

AV's may have more elaborate configurations and additional features than the one shown in FIG. 1, but the AV 10 shown exemplifies the typical features and basic configuration of an AV. That is, the forward open orifice 14 provides an entrance for the penis of the animal whose semen is collected. The rear open orifice 16 provides an exit for the collected semen to a collection device (not shown), most usually through a filter (also not shown).

The AV 10 is, of course, of a size suitable for the subject animal. The dimensions of the AV shown in FIG. 1 are suitable for horses. The AV 10 would have a length of 36 inches, the intromission orifice 14 would have a diameter of 4–5 inches, and the rear portion 18 of the AV 10 would taper down to an exit collection orifice 16 of a diameter of 1.75 inches.

Figure 2:
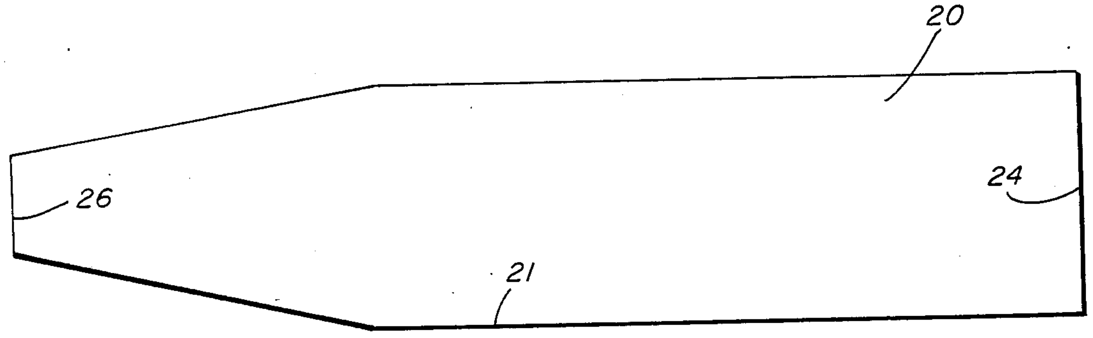
FIG. 2 is an elevation view of a liner constructed according to one aspect of the invention.

FIG. 2 shows a liner 20 for the AV of FIG. 1. The liner 20 is a hollow tubular sheet 21 of plastic film of a generally cylindrical shape, conforming generally to the shape of the interior cavity 22 of the AV 10. The shape is used for ease of manufacture, the sheet 21 being selected to be thin and flexible enough so that the liner 20, once it is inserted into the AV 10, may conform exactly to the internal configuration of the AV 10. The liner 20 shown in FIG. 2, for example, which is for use in the AV of FIG. 1, has a length of 36 inches, an intromission opening 24 at one end with a diameter of 4–5 inches, and a collection opening 26 at the other end with a diameter of 2 inches. The cylindrical shape of the liner 20 extends back from the intromission opening 24 for about two-thirds of the length, and then tapers down in the last third to the smaller collection opening 26.

The liner sheet 21 is preferably plastic film of a suitable thickness that provides strength, flexibility, and the capacity for sterilization. For example, a 3 mil thick sheet of polyurethane or polyethylene copolymer, mylar, polyvinyl chloride or other appropriate polymer would be adequate.

The liner 20 may be formed into the appropriate shape from the sheet 21 by a conventional method, such as heat-sealing or gluing. In a preferred embodiment, the liner 20 may be extruded into the appropriate shape. Different envelope shapes of the liner 20 may be required to accommodate different styles of equine AV's (e.g. Colorado, Missouri and Nishikawa AV's). Furthermore, while the example given is an equine AV, similar liners would be appropriate in the appropriate size and shape for bovine, hog and other farm animal AV's.

The liner 20 is intended for one-time use. It may be distributed in a package and sterilized, as by chemical treatment or by gamma ray irradiation. In this way, the liner 20 when used will assure a sanitary environment, one probably cleaner than can be obtained by trying to regularly clean and use the AV 10 itself. Instructions for using the liner 20 can be printed on the liner sterilized package or on the liner itself.

Figure 3:
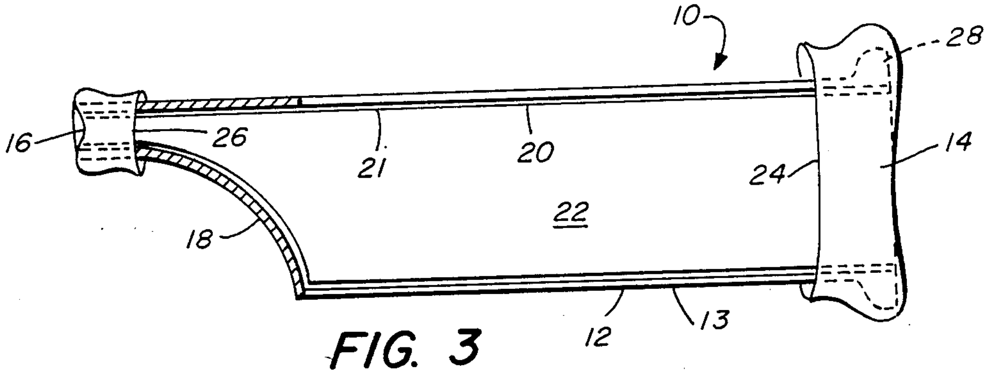
FIG. 3 is an elevational view of the AV of FIG. 1 with the liner of FIG. 2 inserted.

In practice, the thin liner 20 fits inside the AV 10, as shown in FIG. 3, and is the only material coming in contact with the stallion and ejaculate. The small opening 26 at one end of the liner 20, through which the ejaculate can be filtered and removed in the conventional way, fits through the corresponding orifice 16 in the AV 10. The other, or intromission, opening 24 of the liner 20 is arranged over the entrance 14 to the AV 10, and is rolled back over the entrance lip 28. The AV 10 itself is not contacted by the stallion, so that the AV 10 remains sterile during collection.

After collection of the semen sample, the liner 20 can be immediately removed from the AV 10 and be discarded. Another liner can be put in place of the discarded liner and the AV 10 may be immediately used again.

Figure 4:
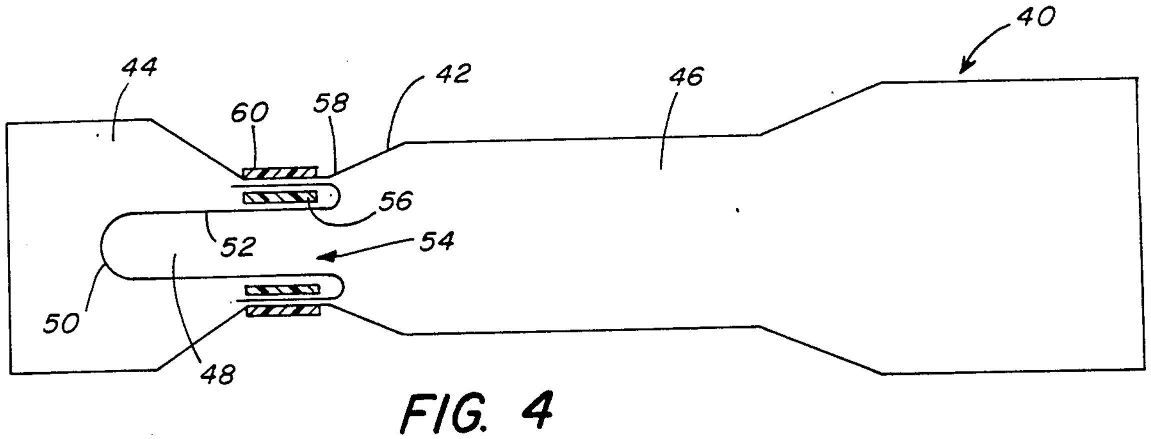
FIG. 4 is an elevation view like that of FIG. 2 of an alternative liner.

The liner 40 shown in FIG. 4 is another form of liner that has special advantages. In the liner 40 shown in FIG. 4, the rear section 42, instead of terminating in a narrow collection opening, extends to form a closed collection chamber 44.

Between the collection chamber 44 and the main portion 46 of the liner 40, within the liner, is located a semen filter 48. The semen filter 48 has a filter portion 50 made up of conventional filtering material common to the art and well known to those who practise the art. The filter 48 includes a flexible wall portion 52 with an open end 54 facing the main portion 46 of the liner, the flexible wall portion 52 being rolled back over a support ring 56 made of a suitable non-toxic plastic or metal. For an AV of the general dimensions described, the support ring 56 would have an outside diameter of approximately 1.25 inches.

The liner 40 includes a reduced diameter section, or constriction 58 where the filter 48 is located, conforming substantially to the outside diameter of the filter. An external, elastic strap 60 surrounds the exterior of the liner constriction 58, tightly binding the constriction 58 and the filter support ring 56, so that the filter 48 is frictionally engaged by the liner 40 at the constriction 58 and secured there. A strap need not be the device for securing the filter 48; a clip or some other device more or less circumferentially surrounding and gripping the ring 56 through the liner constriction 58 may be used also.

Downstream from the constriction 58, the liner 40 enlarges again to form the collection chamber 44.

In practice, the liner 40 is placed inside an AV (such as the one shown in FIG. 1) in a manner similar to that used with the liner 20 described above. Following ejaculation, the semen captured by the AV flows through the filter 48 into the collection chamber 44.

The filtered semen is then removed from the collection chamber 44 by cutting a small hole in the sheet material, preferably plastic film, forming the collection chamber 44, allowing the chamber contents to drain into a specimen cup. The entire disposable liner 40, including the semen filter 48 can then be thrown out.

Thus not only do the AV's not have to be cleaned out after each use, since all contaminated portions are thrown away after each use, but the entire liner, filter and collection chamber can be sterilized as a unit, thereby greatly reducing the problem of cross-infection.

Other modifications of the device and method of the invention besides those suggested in the discussion of the preferred embodiment may be made by those skilled in the art without departing from the scope and spirit of the invention, as set out in the following claims.

What is claimed is:

1. A one-piece disposable artificial vagina liner and collection receptacle comprising:
- a continuous flexible sheet defining
  - a generally tubular main portion having a first and a second end portion,
  - said first end portion defining an intromission opening,
  - said second end portion defining a closed, integral collection chamber, and
- a filter means located within said liner intermediate said main portion and said collection chamber and secured to said sheet,
- said first end portion and said second end portion, and the area disposed therebetween being constructed of the same material and having the same degree of flexiblity.

2. A disposable artificial vagina liner and collection receptacle as claimed in claim 1, wherein said continuous flexible sheet comprises a reduced diameter portion intermediate said main portion and said collection chamber, said filter means comprising a cylindrical element secured to said reduced diameter portion.

3. A disposable artificial vagina liner and collection receptacle as claimed in claim 2, further including exterior filter securing means comprising a circumferential element at least partially surrounding and frictionally engaging said filter means through said flexible sheet.

4. A disposable artificial vagina liner and collection receptacle as claimed in claim 3, wherein said filter means includes a ring means, and said exterior filter securing means comprises a circumferential strap means.

5. An artificial vagina system for the collection of semen from a male animal, comprising:
- a hollow, generally tubular, case having an intromission orifice and an inside wall, and
- a one-piece, disposable sheet liner removably covering said inside wall having sufficient flexiblity to readily conform to the inner wall of said tubular case, said liner comprising a continuous sheet including
- a generally tubular main section having a first and a second end, and defining an intromission opening at said first end,
- a closed, integral collection chamber at said second end, said first and second end portions and the area disposed therebetween being constructed of the same material and having the same degree of flexibility,
- a reduced diameter section intermediate said main sections and said collection chamber, and
- a filter means secured to said reduced diameter section within said liner and defining a hygienic filtered flow path to said collection chamber.

* * * * *